United States Patent [19]

Weinstein et al.

[11] Patent Number: 5,234,621

[45] Date of Patent: Aug. 10, 1993

[54] RINSE-FREE SHAMPOO CONTAINING CROSS-LINKED CARBOXYMETHYLCELLULOSE

[75] Inventors: Benjamin Weinstein, Vineland, N.J.; Donald F. H. Wallach, Hollis, N.H.

[73] Assignee: Micro Vesicular Systems, Inc., Nashua, N.H.

[21] Appl. No.: 809,230

[22] Filed: Dec. 17, 1991

Related U.S. Application Data

[63] Continuation of Ser. No. 553,864, Jul. 17, 1990, abandoned, which is a continuation-in-part of Ser. No. 320,944, Mar. 9, 1989, Pat. No. 4,959,341, and a continuation-in-part of Ser. No. 490,356, Mar. 8, 1990, Pat. No. 4,952,550.

[51] Int. Cl.$^5$ .......................... C11D 9/22; C11D 1/12
[52] U.S. Cl. .......................... 252/174.17; 252/174.18; 252/174.23; 252/174.24; 252/132; 252/544; 252/550; 252/173; 252/DIG. 2; 252/DIG. 13
[58] Field of Search .................. 252/174.17, 174.18, 252/174.23, 174.24, 132, 544, 550, 123, DIG. 2, DIG. 13

[56] References Cited

U.S. PATENT DOCUMENTS

| | | | |
|---|---|---|---|
| 3,969,280 | 7/1976 | Sayce et al. | 252/522 |
| 4,090,013 | 5/1978 | Ganslaw et al. | 526/15 |
| 4,160,063 | 7/1979 | Titus | 428/389 |
| 4,486,335 | 12/1984 | Majewicz | 252/315.3 |
| 4,610,678 | 9/1986 | Weisman et al. | 604/368 |
| 4,786,415 | 11/1988 | Shibata et al. | 210/635 |
| 4,802,997 | 2/1989 | Fox et al. | 252/8.6 |
| 4,812,486 | 3/1989 | Hosokawa et al. | 521/139 |
| 4,826,805 | 5/1989 | Lesniak et al. | 521/53 |
| 4,952,550 | 8/1990 | Wallach et al. | 502/404 |
| 4,959,341 | 9/1990 | Wallach | 502/404 |
| 5,073,202 | 12/1991 | Wallach | 210/660 |

FOREIGN PATENT DOCUMENTS 1152483 8/1983 Canada.

OTHER PUBLICATIONS

McCutcheon's Detergents and Emulsifiers, Allured Publishing Corp., 1970 Annual, pp. 99 and 223.

Primary Examiner—Anthony McFarlane
Assistant Examiner—Nhat D. Phan

[57] ABSTRACT

A new rinse-free shampoo has been developed. The shampoo includes a biodegradable absorbent formed of a cross-linked carboxymethylcellulose which allows a higher water content than conventional shampoos. The soaps used in the shampoo to provide the cleaning action are preferably lauric acid derivatives, including ammonium derivatives. The shampoo leaves less residue than conventional rinse-free shampoos.

3 Claims, No Drawings

RINSE-FREE SHAMPOO CONTAINING CROSS-LINKED CARBOXYMETHYLCELLULOSE

Reference to Related Applications

The present application is a continuation of application Ser. No. 553,864, filed Jul. 17, 1990, now abandoned, which is a continuation-in-part of U.S. patent application Ser. No 320,944, entitled "Biodegradable Superabsorbing Sponge," filed Mar. 9, 1989, now U.S. Pat. No. 4,959,341, and a continuation-in-part of U.S. patent application Ser. No. 490,356, entitled "Particulate Absorbent Material," filed Mar. 8, 1990, now U.S. Pat. No. 4,952,550 the disclosures of which are incorporated herein by reference.

BACKGROUND OF THE INVENTION

The present invention relates to a new cleansing agent such as a shampoo. More particularly, this invention concerns a rinse-free shampoo which leaves less residue than conventional rinse-free shampoos and has a higher aqueous content.

Convention shampoos are made, primarily, of water, cleansing agents such as sodium dodecyl sulfate, thickeners, foam boosters, and fragrance. While these shampoos provide perfectly acceptable hair cleansing in most circumstances, they require a great deal of water to rinse the shampoo out of the hair. In most circumstances this is acceptable but rinsing is a serious problem for the infirm, e.g., geriatric patients and those otherwise hospitalized. While appearance is still an important factor to these people, they are often bedridden so they cannot easily use conventional means of washing their hair. Accordingly, "rinse-free" shampoos were developed several years ago. Rinse-free shampoos are used by rubbing into the hair, thereby entrapping or chelating the dirt particles and oils, and are removed by toweling and/or combing or brushing the hair. The term "rinse-free shampoo," as used herein, means a shampoo which requires little or no additional liquid for its operation.

Although the early rinse-free shampoos had some success, they has two major problems first, they did not clean hair as well as conventional shampoos; and second, they were apt to leave a large amount of residue on the hair. This residue, which may include chelated dirt, particulates from the shampoo itself, or other particulate forms, leaves the hair with a dull, unclean appearance, prevents the pleasing appearance sought by the consumer, and can lead to itchiness and scratching of the scalp. Further, the early shampoos washed away many of the natural oils.

The early rinse-free shampoos had sodium lauryl sulfate as their primary ingredient since the addition of ammonium ions gave problems with residue. Present rinse-free shampoos use materials such as triethanolamide lauryl sulfate, propylene glycol, and a small amount of cocamide diethanolamine. However, these formula modifications have not solved the problems caused by the residue, particularly the resultant greasy and/or gritty feeling of the hair.

Accordingly, an object of the invention is to provide a rinse-free shampoo which is inexpensive yet solves the problems of residue build-up and provides a clean, shiny appearance to the hair.

A further object of the invention is to provide a biodegradable rinse-free shampoo which can be used for camping or other purposes where a conventional shampoo is not convenient.

A further object of the invention is to provide a shampoo for geriatric and other infirm patients.

These and other objects and features of the invention will be apparent from the following description.

SUMMARY OF THE INVENTION

The present invention features a personal cleaner such as a shampoo which contains a gel-like absorbent and has high water content. When used as a shampoo, it can act in a rinse-free mode without leaving significant residue on the hair, thus provides better cleansing action than conventional rinse-free shampoos.

The personal cleaner of the invention has its primary ingredients a carboxylated cellulosic material which is cross-linked and stabilized, preferably by an organo-metallic cross-linking agent, a soap, and water. This personal cleaner is preferably in the form of a shampoo, most preferably a rinse-free shampoo. The preferred carboxylated cellulosic material is carboxymethylcellulose, particularly a carboxymethylcellulose having a high DS (Degree of Substitution) value, most preferably 0.5 or greater. Preferred organo-metallic cross-linking agents are those which contain an aluminum complex such as aluminum acetate stabilized by boric acid. While other metallic ions such as ferric ions may be used, the aluminum ions appear to provide the best cross-linking.

Although any soap could be used in the shampoo of the invention, the preferred soap is a lauric acid derivative such as lauric acid itself, sodium lauryl sulfate, ammonium lauryl sulfosuccinate, lauramides, lauramide diethanolamine, lauryl betaines, and mixtures thereof. Other amides, diethanolamides, chlorides or sulfates of lauric acid could be used as well.

The preferred shampoo has a high aqueous content, with water providing more than 90% by weight of the shampoo. This high water content and the resultant low solid content allows proper cleaning while leaving little residue on the hair.

Further features on the invention will be explained in connection with the following description.

DETAILED DESCRIPTION OF THE INVENTION

The shampoo of the present invention provides excellent cleaning action without residue build-up even in circumstances where it is used in a rinse-free mode, e.g., there is no water rinse used to remove the shampoo. This is accomplished by the high water content (low solid content) of the shampoo and the absorbent gel which entraps the dirt without leaving residue. This high water content means that the shampoo and the entrapped dirt are easily removed by toweling and/or combing the hair.

The shampoo of the invention is based on the use of a cross-linked, carboxylated cellulosic material which acts as an absorbent. This absorbent has a high capacity for holding aqueous solutions so that a higher water content can be used without making the shampoo "runny." This absorbent is biodegradable and substantially nonallergenic. Further details concerning this absorbent are described in U.S. Pat. No. 4,959,341 and U.S. Pat. No. 4,952,550, previously incorporated by reference.

While any soap could be used in the present shampoo, the lauric acid derivatives are preferred. Certain of these soaps, e.g., sodium lauryl sulfate, are commonly used in shampoos. In addition, the shampoo may contain a variety of other materials including stabilizers, conditioners, foam boosters, and fragrances.

The following non-limiting example will further illustrate the invention.

EXAMPLE

In this Example, a "rinse-free" shampoo was made using primarily carboxymethylcellulose, sodium ammonium lauryl sulfosuccinate, and sodium lauric betaine, and water. This shampoo is stable and only a small amount, e.g., a teaspoon is needed to be added to the hair for cleansing purposes.

The shampoo was made as a two-part formulation to obtain the best product. While this procedure is not entirely necessary, it ensures limited air entrapment and stabilization of heat labile materials.

First, the carboxymethylcellulose ("CMC"), preferably a high DS CMC such as Aqualon 7HF, is dry blended with a cross-linking agent, e.g., aluminum acetate stabilized with boric acid, by geometric dilution to insure complete mixing. In the example of the formulation, 1.5% Aqualon 7HF was blended with 0.035% aluminum acetate stabilized with boric acid in a dry vessel. (All percentages are approximate and based on the final weight of the shampoo.) Deionized water (96.5%) is added to a jacketed stainless steel kettle equipped with a blade mixer and is heated to 70-80° C. while stirring, e.g., by passing steam through the jacket. Two preservatives, methyl paraben (0.2%) and propyl paraben (0.03%), are added to the water. Conditioners such as d-panthanol, ceytl alcohol, and stearyl alcohol may also be added at 0.3-0.5% of the total weight. The solution is stirred until the preservatives are completely dissolved. The resulting solution is then transferred to another stainless steel vessel fitted with an homogeneous mixer and is allowed to cool until approximately 60° C. The CMC/cross-linker powder is then added at high speed mixing to insure there is no lump formation and mixed until homogeneous. This resulting material is allowed to sit, e.g., overnight, to minimize the air bubbles in the final product. The CMC is cross-linked by the aluminum acetate/borate and swells with the aqueous solution.

The other part of the shampoo uses a mixture of cleansers, foam boosters, thickeners, conditioners, and fragrance to yield the cleaning action and a more "shampoo-like" texture. Approximately 0.7% of a 40% solution of ammonium lauryl sulfosuccinate in water (Monamate LNT 40-MONA), approximately 0.125% lauramide diethanolamine (Monamid 1089-MONA), 0.375% sodium lauryl betaine (Monateric 985A-MONA), 0.5% propylene glycol, and 0.075% fragrance are blended together. The Monamate LNT 40 and Monateric 985A are soaps, e.g., amphoteric surfactants, while the Monamid 1089 is a foam booster which also may act as a conditioner. The propylene glycol is used primarily as a thickener so as to give a more conventional shampoo-like consistency. Once these ingredients are all blended, they are added to the cross-linked CMC-water mixture at slow speed and mixed slowly to ensure that there is no air entrapment.

For use the shampoo is a rinse-free mode, approximately a teaspoon of the shampoo is put in the hair and rubbed in vigorously. After being allowed to set for several minutes, the shampoo is removed by toweling and/or brushing or combing, leaving clean, manageable hair. The shampoo also could be used as a conventional shampoo.

Other materials and embodiments useful in the present invention are known by those skilled in the art. For example, although the primary use of the cleaner is as a shampoo, it can be used to remove dirt or oil from hands or other surfaces. Accordingly, such other materials and embodiments thereof are included within the following claims.

What is claimed is:

1. A liquid shampoo containing a hydrogel absorbent which entraps dirt without leaving any substantial residue comprising:
   a carboxymethylcellulose cross-linked and stabilized by an organo-metallic cross-linking agent;
   a lauric acid derivative selected from the group consisting of lauric acid, sodium lauryl sulfate, ammonium lauryl sulfosuccinate, lauramide, lauramide diethanolamine, sodium lauryl betaine, and mixtures thereof; and
   at least 90% by weight water;
   wherein no rinse water is needed to remove the shampoo.

2. The shampoo of claim 1 wherein said organo-metallic cross-linking agent comprises an aluminum complex.

3. The shampoo of claim 2 wherein said aluminum complex comprises aluminum acetate stabilized with boric acid.

* * * * *